United States Patent [19]

Kishii

[11] 4,353,649

[45] Oct. 12, 1982

[54] APPARATUS FOR SURFACE STRESS MEASUREMENT OF GLASS COATING AND TRANSPARENT PLASTIC PRODUCT

[75] Inventor: Toru Kishii, Tokyo, Japan

[73] Assignee: Tokyo Shibaura Denki Kabushiki Kaisha, Kanagawa, Japan

[21] Appl. No.: 164,496

[22] Filed: Jul. 2, 1980

[30] Foreign Application Priority Data

Jul. 6, 1979 [JP] Japan .................................. 54-84924
Dec. 10, 1979 [JP] Japan ................................ 54-159133

[51] Int. Cl.$^3$ .......................................... G01B 11/18
[52] U.S. Cl. ...................................... 356/33; 73/800; 356/137
[58] Field of Search .................... 356/32, 33, 34, 35, 356/130, 135, 136, 137; 73/800

[56] References Cited

U.S. PATENT DOCUMENTS 3,449,051  6/1969  Levitt ................................. 356/135
3,510,222  5/1970  Shaw, Jr. ............................. 356/33
4,207,000  6/1980  Miller .................................. 356/33

Primary Examiner—Vincent P. McGraw
Attorney, Agent, or Firm—Schwartz, Jeffery, Schwaab, Mack, Blumenthal & Koch

[57] ABSTRACT

Disclosed is an apparatus for measuring surface stress of glass coating and transparent plastic product, which comprises means for projecting the coherent light on the surface of the object to be measured, an output prism having a refractive index greater than that of said surface, mounted proximal to the light incident point on said surface in such a manner that one face thereof is in optically close contact with said surface, a telescope to measure the critical angle at the interface of said surface and said output prism in respect of the projected light from said output prism, and a polarizer located on the optical path of said projected light. The apparatus facilitates easily a direct and non-destructive measurement of the surface stress without any complex calculation.

13 Claims, 5 Drawing Figures

APPARATUS FOR SURFACE STRESS MEASUREMENT OF GLASS COATING AND TRANSPARENT PLASTIC PRODUCT

BACKGROUND OF THE INVENTION

The present invention relates to an apparatus for measuring surface stresses, and more particularly, to an apparatus for measuring surface stresses of glass coatings and transparent plastic products.

The term, glass coating, as used herein means enamelling given to the surface of copper instruments, enamelled surface of cast iron goods, enamel finishes for aluminum, brass, copper and other surfaces, and glazes for cloisonne, ceramics and procelain, all those products used mainly in daily life. The surface stress of these coatings plays significant roles in the quality and the decorative purposes of the products in the following points:

Firstly, it is necessary for these coatings to have an optimum compression stress in order for the coating to adhere well to the base and to have an excellent resistance against thermal and mechanical shocks as well as to corrosions by chemicals. If the surface stress is tensile, the cracks easily appear, the surface tends to peel off easily, and the resistance against chemicals becomes inferior. If the surface stress had an excessive compression force, the surfaces are more likely to present the phenomena generally referred to as "peeling" which is a voluntary removal of the surface coating film.

In the case of ceramics, on the other hand, the surface stress of the glaze is used intentionally as a tensile force thereby to cause hair cracks for decorative purposes. Since the designs and fine lines caused by such air cracks are determined depending on the tensile strength, selection of a suitable tensile strength is necessary depending on the purpose.

In the case of plastic products, stress is distributed through-out the entire product surface because of the thermal hysteresis at the time of molding, and non-uniform contraction accompanying the temperature changes after molding. If the stress is excessive, the product may become deformed, or cracks may appear after some years, and that may invite destructions and damages of the products. Solvent cracking phenomenon which is the appearance of cracks caused by the contact with catalysts may often occur.

It is, therefore, considered quite important for quality control that the surface stresses of glass coatings and plastic products by measured.

The present invention aims to provide an apparatus for a speedy and simple non-destructive measurement of the surface stresses of glass coatings and transparent plastic products.

The prior arts for measuring the surface stress of glass coatings and the like are particularly described in the following references:

H. Inada's "Fitness of Glaze and Body", Parts I and II, Interceram, No. 4, P. 397 (1978) and No. 1, P. 19 (1979) respectively describe, as the measurement method of the surface stress of glass coatings for ceramics, a method wherein a thin sample piece is obtained by vertically cutting the object being measured in the direction vertical to the coating surface and the photoelastic effect of the transmitted light is measured. However, this method is a destructive test requiring extra labor and costs, and the stress becomes alleviated in part as the thin test strip is cut out. When the method is applied to measuring the stress of the enamelled layer, the operation is generaly unsuccessful because the enamelled layer would become destroyed during the process of preparing the thin test strips.

Yogyo Kyokai Shi (Journal of Association of Ceramics, Japan), Vol. 72, No. 11-2, pp. 102–106 (1962) (in Japanese), describes a method of a surface stress measurement for enamelled surfaces wherein a thin plate is prepared from the material which is the same as the base to be coated, the enamel is flowed over one surface thereof, fired and then cooled to the room temperature, and the degree of camber of the thin plate appearing then is measured, thereby estimating the surface stress. This method does not measure directly the coating of the object being measured, but merely assumes the surface stress indirectly by measuring the sham test piece prepared separately. This method is not applicable to the case where the base plate is made of materials such as cast iron from which it is difficult to make a thin plate, and where the base plate is made of materials of which thermal expansion property is likely to change by the very small differences in the heat treatment conditions, such as cast iron, alloy steel, and non-ferrous alloys, since the measured values often tend to deviate from the actual surface stress values of the materials being measured.

Thus, neither one of the above-mentioned two measurement methods directly measures the coating surface of the object being measured; they are either the destructive test or the measurement test using sham test pieces and have the defects as above detailed, and therefore not satisfactory as a method of measuring the surface stress of glass coatings.

On the other hand, Acloque, P. and Guillemet, C., in Compt Rend 250 (1960) 4328 discloses a method of measuring the surface stress of thermally tempered glass. Their method utilizes the light propagated as an evanescent wave over the product surface, measuring the differences of photoelastic optical paths (sometimes referred to as retardation) as the function of propagation distance, and seeking the surface stress from the differential regarding the distance. Although this is a non-destructive measurement, it is defective in that exciting the evanescent wave is considered generally difficult, and since it is weak even when excited, it is extremely difficult to measure the differences in the optical paths as the function of the distance. It is further defective in that calculation used in obtaining the stress is complex and impractical.

As for the chemically tempered glass, the inventor of this invention published a paper dealing with a non-destructive method of measuring the surface stress in Yogyo Kyokai Shi 87, [3] 119 (1979) (in Japanese) by utilizing the property of the glass surface layer which has a high refractive index, and the light wave guide effect which propagates the light without scattering. However, the object to be measured for which the present invention is intended has no surface layers with a high refractive index and therefore the above method is not applicable.

Kitano proposed a method of seeking the surface stress of thermally tempered glass from measurement of the critical angle, in Yogyo Kyokai Shi 80, [4], 173, (1972) (in Japanese). This method again is not applicable to the case where the surface is not flat but curved or irregular, or where the surface layer is not uniform or has the light scattering property.

As mentioned above, the conventional technology of measuring the surface stress of glass coatings, transparent plastics, etc. did not obtain the satisfactory measurement values.

SUMMARY OF THE INVENTION

Accordingly, the object of the present invention is to provide an apparatus which enables a direct and non-destructive measurement of the surface stresses of glass coatings, transparent plastic products, etc.

Another object of the present invention is to provide an apparatus to measure surface stresses of glass coatings, transparent plastic products, etc., which does not require complex computations and performs an easy and accurate measurement of the surface stress.

According to the present invention, there is provided an apparatus for measuring surface stress of glass coatings, transparent plastic products, etc. which comprises means for projecting coherent light on the surface of the object to be measured, an output prism having a greater refractive index than that of said surface, mounted proximal to the point of the light incident on said surface in such a manner that one face thereof may be in optically close contract with said surface, a telescope to measure the critical angle of the light from said output prism at the interface of said surface and said output prism, and a polarizer positioned on the optical path of the light from said output prism.

The present invention is based on the fundamental principles explained below: In glass coatings and transparent plastic products, the principal stress perpendicular to the surface is zero since the surface is generally a free surface. Accordingly, the stress is present only in the direction parallel to the surface. In respect of the beams advancing inside such a medium, there is a difference in the refractive indices caused by the photoelastic effect between the beams advancing parallel to the surface, which vibrate in directions parallel with the surface and vertical to the surface. The difference of the refractive indices $\Delta n$ is determined by the formula:

$$\Delta n = C \cdot p$$

wherein;

p is the surface stress (Kg/cm$^2$)

C is a photoelastic constant (Kg/cm$^2$)$^{-1}$

Thus, if the photoelastic constant C is known, the surface stress p may be obtained by seeking the refractive index difference $\Delta n$.

The surface stress measuring apparatus according to the present invention utilizing the above mentioned fundamental principle facilitates obtaining the surface stress by merely seeking the difference of the critical angles of the two polarized lights which advance inside the surface of the object to be measured, providing an extremely simple and speedy measurement.

BRIEF DESCRIPTION OF THE DRAWINGS

The present invention will be described below in more detail with reference to drawings which illustrate preferred embodiments of the invention, in which.

DETAILED DESCRIPTION OF PREFERRED EMBODIMENTS

Figure 1:
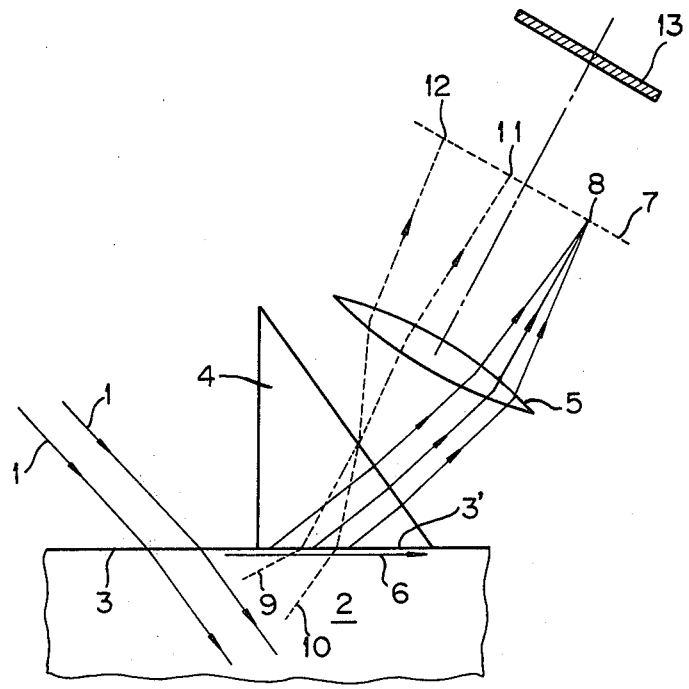
FIG. 1 is a diagram to explain the principle of the present invention.

In FIG. 1, the reference numeral 1 denotes the incident ray (the coherent ray) projected on the surface 3 of the object being measured 2 by a light projecting means (not shown). Numeral 4 denotes an output prism of which one face is in optically close contact with the surface 3, while numeral 5 denotes an objective lens of a telescope.

When the incident light 1 enters the surface 3, it generally scatters. In the case of glass coatings such as enamel and glazings, the light is scattered by the non-uniform portions such as emulsified particles, crystallites, small air bubbles, etc. included in the coating layer. In the case of transparent plastics, such non-uniform portions are limited, but the light tends to scatter at the stage when it enters the surface 3. Allowing for differences of degrees in the scatterings in the glass coatings and the transparent plastic products as above explained, the incident rays do cause scatterings.

Of these scattered lights, the light 6 which advances parallel to the surface 3 within the close proximate portion of the surface 3 (or the surface layer) of the object being measured becomes the critical refractive ray for the boundary surface 3' of the object 2 and the prism 4, taken out at the output prism 4 to be focused at one point 8 on the focal plane 7 of the objective lens 5. The other lights which do not advance in parallel to the surface 3, such as 9 and 10, have an incident angle which is smaller than the critical refractive light when they reach said boundary surface 3', and focus at points 11 and 12 which are located above the point 8 on the focal plane 7. Accordingly, the space above the point 8 on the focal plane 7 is lighter because the light reaches there, while the space below the point 8 is dark because the light does not reach there. Thus, the point 8 becomes the boundary for the dark and the light spaces. The technique of seeking the refractive index from such a boundary of the dark and the light areas is already practically employed in Abbe's refractometer, etc.

Where the surface stress exists in the surface 3, even with the light 6 advancing in parallel to the surface 3, the boundary surface 8 of the dark space and the light space becomes varied with the light vibrating parallel to the surface and the light vibrating perpendicular thereto which has refractive index different from each other. In respect of this two kinds of lights, it is possible to confirm the dark/light boundary areas separately by observing through the polarizer 13 positioned in the rear (or alternately in the front) of the focal plane 7, thereby seeking the difference in the refractive indices $\Delta n$ of the two.

The light projecting means includes a light source of coherent light, examples of which are, gas pulsing tubes for gas lasers or dye lasers considering the intensity of the light, or a gas-discharge lamp, an incandescent lamp, etc. may also be used by letting the projection pass the pin holes. With the enamelled or glazed products and plastic products for every day use, this surface is not generally uniform, and the refractive index within the coating layer is neither uniform, said boundary for the dark and the light areas is not necessarily clear cut, and it is therefore difficult to seek the refractive index differences which are sufficiently precise. The apparatus of the present invention, however, can employ as a standard for the dark/light boundary areas the distinctive patterns consisting of fine interference light spots formed by the lights reaching the focal plane of the objective lens of the telescope, as a result of using the light source of lights which is coherent and may be readily interferred as above discussed. This enables us to obtain the refractive index difference with a sufficient precision.

In the present invention, the role that the light projecting means plays is to excite the scattering light within the close proximate portion of the surface 3 (the surface layer) of the object to be measured, so that any type of means may be used as a rule so long as it can project on to the surface lights which is coherent and may be readily interferred. However, as it is clear from the foregoing explanation, the more the scattered lights advancing in parallel to the surface, the clearer the boundary between the dark and the light areas to be observed by the telescope becomes, and it is therefore most advantageous for measurement. Accordingly, the light projecting means is preferred to be such which can create more scattered lights parallel to the surface. For this purpose a light projecting means should be provided with an input prism with one face thereof being in optically close contact with the surface of the object to be measured, and further said means should be positioned so that the incident angle be substantially equal to the critical angle when the light passes the input prism and enters the surface. Since said critical angle differs depending on the material of the surface, the apparatus should preferably be provided with a means to adjust the projection angle of the light.

The output prism plays the role of taking out the scattered lights created on the surface layer, and is therefore disposed at a point close to the point of the incidence, for instance at a position spaced apart by 0.1 to 10 mm, and where one face thereof may be in optically close contact with the surface. In order to secure the optically close contact, it is desirable to fill the space between the prism and the surface with an immersion liquid of the same or similar refractive index to the prism, such as methylene iodide, ethylene tetrabromide. It is particularly important that such a liquid is used for surfaces with irregularities or curves.

The telescope is for measuring the critical angle by observing the boundary of the dark and the light spaces formed on the focal plane of the objective lens by the critical refractive lights projected by the output prism. Therefore, it is desirable that the optical axis be positioned parallel to the critical refractive light. Since the critical angle differs depending not only on the direction of vibration of the polarized light but also on the surface materials, it is preferable that the apparatus of the present invention be provided with means for adjusting the angle of inclination of the optical axis of the telescope.

The telescope is provided with an ocular micrometer or an ocular lens incorporating a micrometer for a precise measurement of the boundary between the dark and the light spaces formed on the focal plane of the objective lens, thereby achieving the measurement of the critical angle.

An example of the polarizer is an artificial polarizer or a polarizing prism. The polarizer is rotatably positioned on the optical path of the projected light to thereby select and pass arbitrarily the light in the direction of vibration. This polarizer may be attached to the optical path between the objective lens and the ocular micrometer, or between the objective lens and the ocular lens incorporating a micrometer, of the telescope.

According to the apparatus of the present invention, it is quite easy to create the scattered lights parallel to the surface in the surface layer of the object to be measured, and their intensity is sufficient to be taken out by the output prism and observed. Accordingly, the apparatus of the present invention facilitates a direct and non-destructive measurement of the surface stresses of the glass coatings and the transparent plastic products, as well as an easy measurement without any complex calculation.

The above mentioned advantages and other advantages of the present invention will become still more clear by the descriptions given below of the embodiments.

Figure 2:
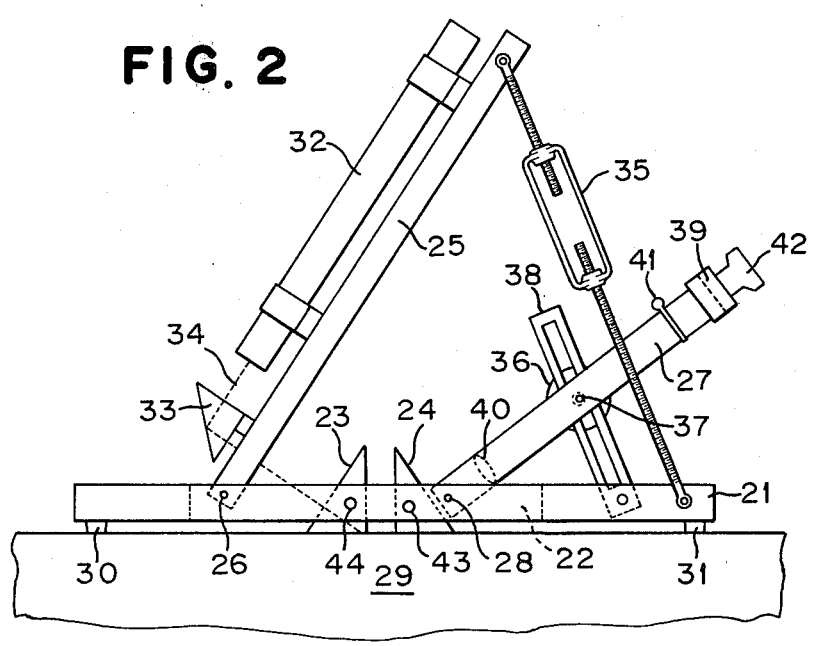
FIG. 2 is an elevational view showing one embodiment of the present invention.

In FIG. 2, there is bored an opening 22 on a frame 21 and there are also provided triangular input prism 23, and output prism 24 with one of their faces opposedly facing each other in close proximity to each other. There are also provided a support axis 26 to rotatably support the laser holder 25 and a support axis 28 to also rotatably support the telescope 27. The frame 21 is further provided with legs 30 and 31 so that one face of each of the prisms 23, 24 may be stably in close contact with the surface of the glass coating layer 29 which is the object to be measured. On the laser holder 25 are disposed a laser tube or a laser pulsing tube 32 which includes a laser tube and a reflection prism 33, and the laser beam 34 issued from the laser pulsing tube 32 as shown in the drawing is redirected by the reflection prism 33 and projected onto the coating layer 29 via the input prism 23. Between the upper end of the laser holder 25 and one end of the frame 21 is provided a turnbuckle mechanism 35 which enables changing the angle of inclination of the laser holder 25 in respect of the support axis 26, and accordingly change the projection angle of the laser beam to the coating layer 29. The telescope 27 is also rotatable in respect of the support axis 28, and may be fixed by suitably adjusting the angle of the inclination of the optical axis by the handle 36 which may be fixed by tightening a screw and the grooved plate 38 which can slide the axis 37 of the handle 36. The telescope 27 is provided with an objective lens 40 focusing the light from the output prism 24 on the focal plane 39. In this case, there is rotatably provided with an artificial polarizer 41 between the objective lens 40 and the focal plane 39, and there is further provided an ocular lens incorporating a micrometer or an ocular micrometer 42 to observe the interfering strip patterns (the boundary of the dark and the light spaces) focused on the focal plane 39. The axes 43, 44 of the prisms 23, 24 are loosely supported within the axial hole provided in the frame 21 with some allowances, and their relative positions may be variably determined according to the surface of the coating 29. In measurement, an immersion liquid having the same or similar refractive index of the prisms 23, 24 is dropped on the surface of the coating 29 in order to secure an optically close contact of the surface of the coating 29 and the prisms 23, 24.

Figure 3:
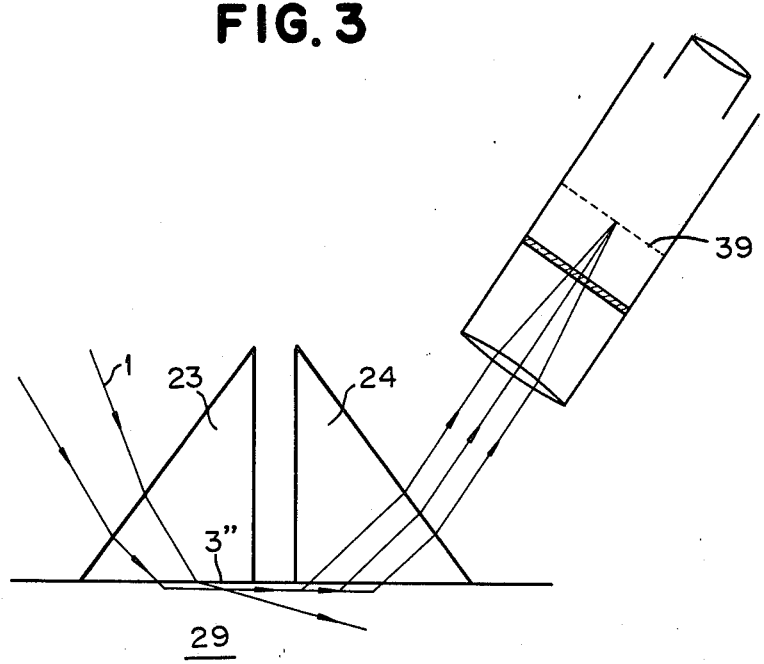
FIG. 3 is a schematic drawing showing a partially enlarged view of FIG. 2.

The input prism 23 in the above mentioned embodiment is not indispensable to the present invention, but its use proves advantageous for measurement since the light injected by the output prism 24 increases. That is, as shown by partially enlarged view in FIG. 3, when the refractive index of the input prism 23 is made greater than that of the coating layer 29, much of the incident light 1 passes near the output prism 24, and the light to be taken out from the output prism 24 and the light reaching the focal plane 39 become greater, thereby facilitating an easy measurement. It is most effective when the incident angle to the interface 3" of the incident light is equal to the critical angle. Thus, it is desirable that the angle of inclination for the laser holder 25 be adjusted accordingly. On the other hand, it is necessary to select the angle of the telescope so as to cause its optical axis to be parallel to the projected light of the critical refractive index.

Figure 4:
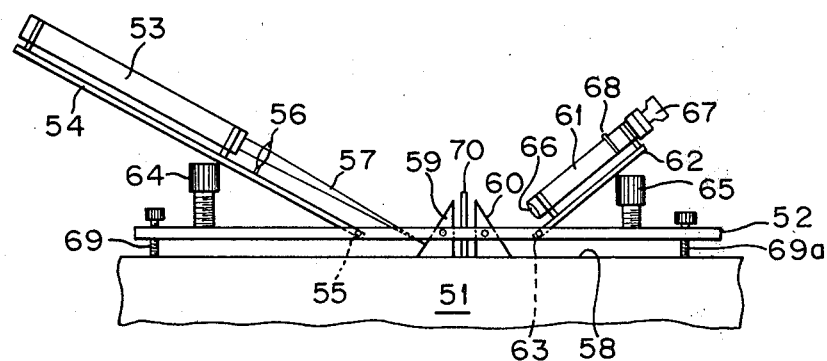
FIG. 4 is an elevational view showing another embodiment of the present invention.

FIG. 4 shows another embodiment of the present invention. On a frame 52 to be placed on the surface of a transparent plastic product 51 or the like, a holder 54 on which is mounted a laser pulsing tube 53 is rotatably supported by the support axis 55, and the light from said laser pulsing tube 53 is transformed into a convergent beam 57 by the convergent lens 56 for projection. The convergent beam 57 projected therefrom passes through an input prism 59 disposed on the frame 52, optically contacting the surface of the transparent plastic product 51. There is, on the other hand, disposed similarly an output prism 60 on the frame 52 in optical contact with the surface 58 of the plastic product 51, said output prism 60 taking out the scattered lights propagating within the surface 58 of the said plastic product 51. On the said frame 52 is also rotatably supported a holder 62 by the support axis 63, on which is mounted a telescope 61 to observe the projected light from the output prism 60. The angles of the holders 54, 62 respectively carrying said laser pulsing tube 53 and the telescope 61 may be adjusted arbitrarily by the support screws 64, 65 attached to the frame 52 so that the incident angle to the surface 58 may be made equal to the critical angle and the optical axis of the telescope 61 may be made parallel to the projected light of the critical refractive index. The telescope 61 is provided with an objective lens 66 and an ocular micrometer 67, and further is provided with an artificial polarizer 68 therebetween.

The frame 52 is provided with threaded legs 69, 69a for adjusting the distance to the surface 58. Between the prism 59 and the prism 60 is provided a screen 70 to shut off the unnecessary light.

Laser beams emitted from the laser pulsing tube 53 are converged by the convergence lens 56. The incident angle for the converged beams is adjusted by changing the angle of inclination of the holder 54 by the aid of the screw 64. The laser beams then enter the surface 58 of the transparent plastic product 51 via the input prism 59 at a desired angle. The incident lights are scattered in the surface layer of the transparent plastic product 51 and propagated. As explained hereinbefore, the scattered lights are taken out by the output prism 60 and converged on a predetermined focal plane by the objective lens 66 of the telescope 61. As the polarized light vibrating perpendicularly to the surface 58 and the polarized light vibrating in parallel therewith form separate boundaries of the dark and the light areas on the focal plane, and the surface stress may be sought in the same way as in the foregoing embodiment.

Figure 5:
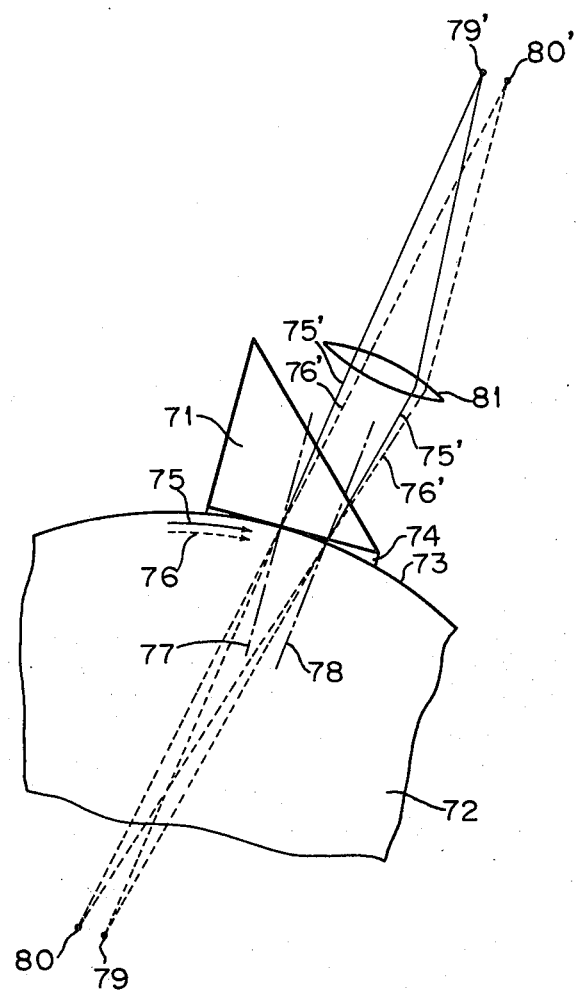
FIG. 5 is an explanatory drawing to show measurement of the surface stress of a spherical or curved surface.

In the above-mentioned two embodiments, referred to is the instance where the surface of the object to be measured is substantially flat. However, the measurement of a curved surface may similarly be performed. That is, as shown in FIG. 5, the output prism 71 is held opposedly in contact with the surface 73 of the object 72 to be measured, and the void is filled with an immersion liquid 74 having the same or similar refractive index as that of the output prism 71. This will achieve the propagation of light in parallel to the surface within the surface layer of the object to be measured, and the two polarized lights 75, 76 vibrating in the directions crossing at right angles with each other may be taken out accurately and optimaly, and the lights 75', 76' taken out from these polarized lights 75, 76 are projected respectively from the curved surfaces 73 with prescribed angles to the perpendiculars 77, 78. In this state, the lights advances taking the same route as if they have been ejected respectively from the points 79 and 80. If the objective lens 81 of the telescope is replaced with a lens having a focal length focusing real images for the points 79 and 80 within the ocular micrometer, the virtual images will be formed at the points 79', 80'. The scattered lights not in parallel to the surface are converged above the point 79' or the point 80', so that the point 79' or the point 80' also becomes the border for the dark and the light areas. The points 79' and 80' are still formed on the focal plane of the objective lens used in the case where the object being measured is of a flat surface, and thus measurement of the surface stress is possible as in the said case. It then becomes possible to seek the surface stress of the surface being measured by measuring the positions of the points 79' and 80' by the ocular micrometer.

I claim:

1. An apparatus for measuring surface stress of glass coating and transparent plastic products, comprising means for projecting coherent light to provide scattered light in the surface layer of the object to be measured, an output prism having a refractive index greater than that of said surface, mounted proximal to the light incident point on said surface in such a manner that one face thereof is in optically close contact with said surface, a telescope to measure the critical angle at the interface of said surface and said output prism in respect of the projected light from said output prism, and a means, including a polarizer located on the optical path of said projected light downstream of said output prism, for observing interference light spots formed at a focal plane of an objective lens of the telescope.

2. The apparatus as claimed in claim 1, wherein the light projecting means is provided with a gas laser pulsing tube or a dye laser pulsing tube as a light source for lights which is coherent and may be readily interfered.

3. The apparatus as claimed in claim 1, wherein the light projecting means is a prism to guide the light from the light source onto the surface of the object to be measured and includes an input prism having a refractive index greater than said surface, mounted in such a manner that one face thereof may be in optically close contact with said surface.

4. The apparatus as claimed in claim 3, wherein the light projecting means is so disposed that the incident angle becomes substantially equal to the critical angle when the light passes the input prism and enters the surface of the object to be measured.

5. The apparatus as claimed in claim 1, wherein the telescope is disposed in such a manner that its optical axis will become parallel to the projected light with critical angle of refraction.

6. The apparatus as claimed in claim 1 or claim 5, wherein the telescope is provided with an ocular micrometer.

7. The apparatus as claimed in claim 1 or claim 5, wherein the telescope is provided with an ocular lens incorporating a micrometer.

8. The apparatus as claimed in claim 1, wherein the polarizer is rotatably positioned on the optical path between the objective lens and the ocular micrometer or the ocular lens incorporating a micrometer of the telescope.

9. The apparatus as claimed in claim 1 or claim 8, wherein the polarizer is an artificial polarizer.

10. The apparatus as claimed in claim 1 or claim 8, wherein the polarizer is a polarizing prism.

11. The apparatus as claimed in claim 1, further comprising means for adjusting the projection angle of the incident lights to be projected on the surface of the object to be measured.

12. The apparatus as claimed in claim 1, further comprising means for adjusting the inclination angle of the optical axis of the telescope.

13. A method for measuring surface stress of glass coating and transparent plastic products, comprising projecting a coherent light on the surface of the object to be measured to provide scattered light in the surface layer thereof;

taking out said scattered light by an output prism having a refractive index greater than that of said surface and mounted proximal to the light incident point on said surface in such a manner that one face thereof is in optically close contact with said surface; and measuring the critical angle at the interface of said surface and said output prism in respect of the projected light taken out of said output prism, by means of a telescope provided with a polarizer for observing interference light spots formed by the light reaching the focal plane of an objective lens of said telescope.

* * * * *